United States Patent [19]

Yabuuchi et al.

[11] Patent Number: 5,407,806
[45] Date of Patent: Apr. 18, 1995

[54] METHOD FOR QUANTITATIVELY MEASURING SUGAR-ALCOHOL, COLUMN AND KIT THEREFOR

[75] Inventors: Masahiko Yabuuchi, Omiya; Hiroshi Akanuma, Yokohama; Minoru Masuda, Ageo; Kazuo Katoh, Kobe; Tsuneo Nakamura, Omiya; Shigeru Tajima, Fujioka; Masashi Hashiba, Gunma; Hiroshi Hayami; Tomoko Takezawa, both of Fujioka; Masachika Hirayama, Omiya, all of Japan

[73] Assignee: Nippon Kayaku Kabushiki Kaisha, Tokyo, Japan

[21] Appl. No.: 7,656

[22] Filed: Jan. 22, 1993

Related U.S. Application Data

[63] Continuation of Ser. No. 504,659, Apr. 4, 1990, abandoned.

[30] Foreign Application Priority Data

Apr. 10, 1989 [JP] Japan .................................. 1-087963
Apr. 26, 1989 [JP] Japan .................................. 1-104712

[51] Int. Cl.$^6$ ............................................. C12Q 1/26
[52] U.S. Cl. ........................................... 435/25; 435/4; 435/28; 435/105; 435/803; 435/810; 436/174; 436/177; 436/178; 436/815; 210/656; 210/661

[58] Field of Search ..................... 435/4, 25, 28, 105, 435/803, 810; 436/174, 177, 178, 815; 210/656, 661

[56] References Cited

U.S. PATENT DOCUMENTS 3,864,166  2/1975  Barker et al. ...................... 127/46 R
4,810,640  3/1989  Nakamura et al. .................... 435/25
4,994,377  2/1991  Nakamura et al. .................... 435/25

OTHER PUBLICATIONS

*Ion Exchange Chromatography* (1983) published by Pharmacea Fine Chemicals, Uppsala, Sweden, pp. 1–11.

Primary Examiner—Margaret Parr
Assistant Examiner—Ardin H. Marschel
Attorney, Agent, or Firm—Nields & Lemack

[57] ABSTRACT

A present invention relates to a method for quantitatively determining sugar-alcohols characterized by passing test samples containing sugar-alcohols, proteins, and saccharides through a column filled with basic anion-exchange resins which have a protein-removing ability and a saccharide-removing ability, and then quantitaing the sugar-alcohols in the effluent out of the column, a column filled with said resins and an aqueous solution of boric acid, and a kit. Sugar-alcohols such as 1,5-anhydroglucitol and the like have been calling attention as markers for diabetes mellitus recently.

22 Claims, 5 Drawing Sheets

METHOD FOR QUANTITATIVELY MEASURING SUGAR-ALCOHOL, COLUMN AND KIT THEREFOR

This application is a continuation of application Ser. No. 504,659, filed Apr. 4, 1990, now abandoned.

BACKGROUND OF THE INVENTION

1. Field of the Invention

The present invention relates to a method for measuring quantitatively sugar-alcohols, a column and a kit for the process.

2. Description of the Prior Art

Sugar-alcohols substances such as 1,5-anhydroglucitol (referred to as AG hereafter) and myo-inositol (referred to as MI hereafter) have been receiving attention in recent years as markers for the diagnosis of diabetes mellitus.

In quantitative analysis of sugar-alcohols in human body fluid, there have been used extracts which have been freed of interfering substances such as saccharides (particularly, glucose) and proteins which are generally contained abundantly in the human biological fluid and which have an influence on the analysis.

Removal of the aforementioned interfering substances, particularly proteins has required heretofore centrifugal separation, and is troublesome. Especially, taking account of clinical applications, simplification of the removal operation has been desired. It is preferred for quantitative analysis of sugar-alcohols in a number of test samples to remove simultaneously saccharides and proteins.

Techniques for determining sugar-alcohols in blood have been heretofore proposed, including the measurement of protein-freed serum or plasma, after converting them to derivatives, on gas chromatography (abbreviated to a GC method hereafter), or the measurement of AG in effluents from an interfering substance-removing column, through which protein-freed test samples have been passed, using an enzyme colorimeter (abbreviated to an enzyme colorimetric method hereafter) (EP 261591-A).

The GC method involves a protein-removing step and a derivative-producing step before subjecting the sample to gas chromatography, and requires several column chromatographic operations and condensing to dryness operations so that it requires many handlings, is time consuming and is unsuitable for measuring a number of test samples. Depending upon the samples, there are cases where undeterminable peaks overlap with sugar-alcohol peaks rendering the resulting measurements inaccurate.

The enzyme colorimetric method comprises passing protein-freed samples through an interfering substance-removing column to remove the interfering substances, primarily saccharides, and oxidizing AG with oxygen simultaneously producing hydrogen peroxide, an amount of which is quantitatively determined after coloration with enzyme by a colorimetric measurement. Comparing with the GC method, it has fewer steps, and is capable of treating a large number of samples so that it may be regarded as an excellent method. For clinical examination, however, it involves some time-consuming troublesome steps requiring many handlings with the coloration step taking a long time to reach a stable state, so that the number of samples measurable by one operator is limited. Either one of the aforementioned two methods is very time-consuming with many handlings in determination of sugar-alcohols, and can not be easily conducted for the measurement.

In order to overcome the difficulties as described above, the present inventors have made a research on a method for automating the measurement of sugar-alcohols, and discovered that even when samples of serum or blood plasma are injected sequentially into an interfering substance-removing column, through which water or the like is allowed to steadily flow, as an apparatus for directly measuring them, the interfering substances can be completely removed to permit determination of the sugar-alcohols. Moreover, we have made a column and a kit for use in the measurement. The present invention has been accomplished on the basis of the above discoveries.

SUMMARY OF THE INVENTION

In the first embodiment of the present invention, there is provided a method for quantitatively determining sugar-alcohols characterized by passing test samples containing sugar-alcohols, proteins, and saccharides through a column filled with basic anion-exchange resins which have a protein-removing ability and a saccharide-removing ability, and then quantitating the sugar-alcohols in the effluent out of the column.

In the second embodiment of the present invention, there is provided a column for removing proteins and saccharides filled with strongly basic anion-exchange resins and an aqueous solution of boric acid, said resins comprising hydrophilic polymer resins having no aromatic ring and having quaternary ammonium groups.

In the third embodiment of the present invention, there is provided a kit comprising a column filled with basic anion-exchange resins having a protein-removing ability and a saccharide-removing ability and with an aqueous solution of boric acid, a reagent for quantitating sugar-alcohols, and a sugar-alcohol for preparing calibration curves.

In the fourth embodiment of the present invention, there is provided a method for determining quantitatively sugar-alcohols characterized by ① adding a protein-insolubilizing agent capable of producing oily precipitates to test samples containing sugar-alcohols, proteins, and saccharides to settle the proteins as oily precipitates as well as to produce a supernatant liquid, and then passing the supernatant liquid through a column filled with protein-insolubilizing agent-adsorbing resins and basic anion-exchange resins, or by ② adding a protein-precipitating agent and a protein-denaturizing agent to said test samples to precipitate the proteins as water insoluble materials, and passing the precipitated liquid through a column filled with basic anion-exchange resins, and thereafter quantitating the sugar-alcohols in the resultant effluent.

In the fifth embodiment of the present invention, there is provided a method for determining quantitatively AG in blood characterized by injecting sequentially a number of test samples into an apparatus comprising an interfering substance-removing column through which a liquid flows, an injector, and a biosensor.

BRIEF DESCRIPTION OF THE DRAWINGS

FIG. 1-2 shows an AG calibration line obtained by using L-sorbose oxidase,

FIG. 1-3 shows an MI calibration line obtained by using myo-inositol dehydrogenase, FIG. 1-4 shows a relationship between measurements of the serum, which has been treated by the fourth embodiment-② of the present invention as defined above, using pyranose oxidase and those using gas-chromatography, FIG. 1-5 shows a relationship between measurements of the serum, which has been treated by the fourth embodiment-① of the present invention as defined above, using pyranose oxidase and those using gas-chromatography, FIG. 1-6 shows a relationship between measurements of the serum, which has been treated by the first embodiment of the present invention as described above, using pyranose oxidase and those using gas-chromatography, and FIGS. 2-1 through 2-3 show relationships between measurements of AG in the serum by the systems of Examples 2-1 through 2-3 and those by the GC method, respectively.

DETAILED DESCRIPTION OF THE INVENTION

Figures 1, 2:
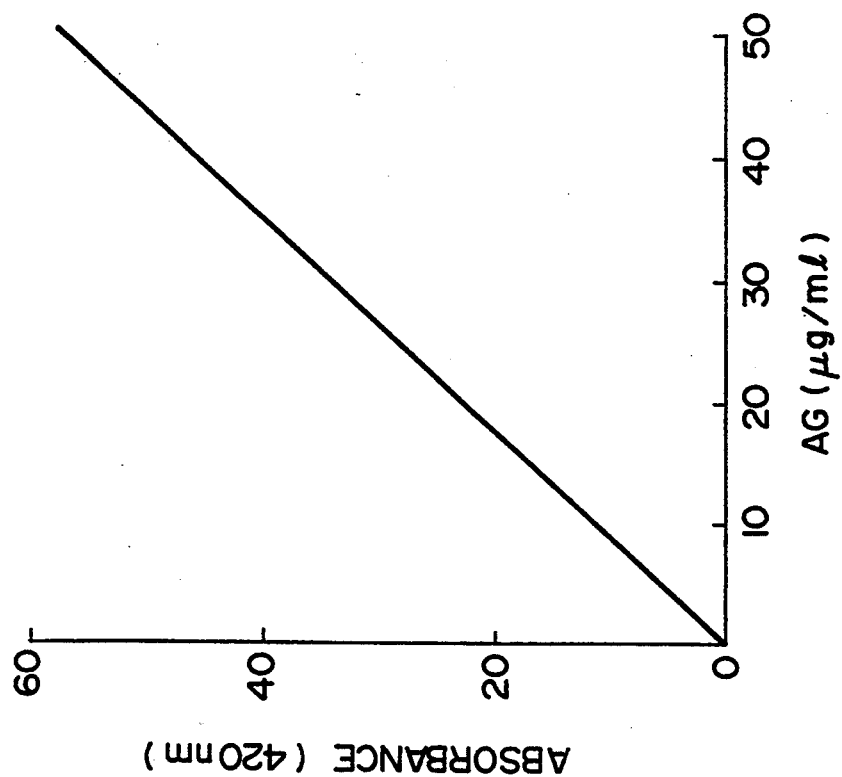
Figure 1:
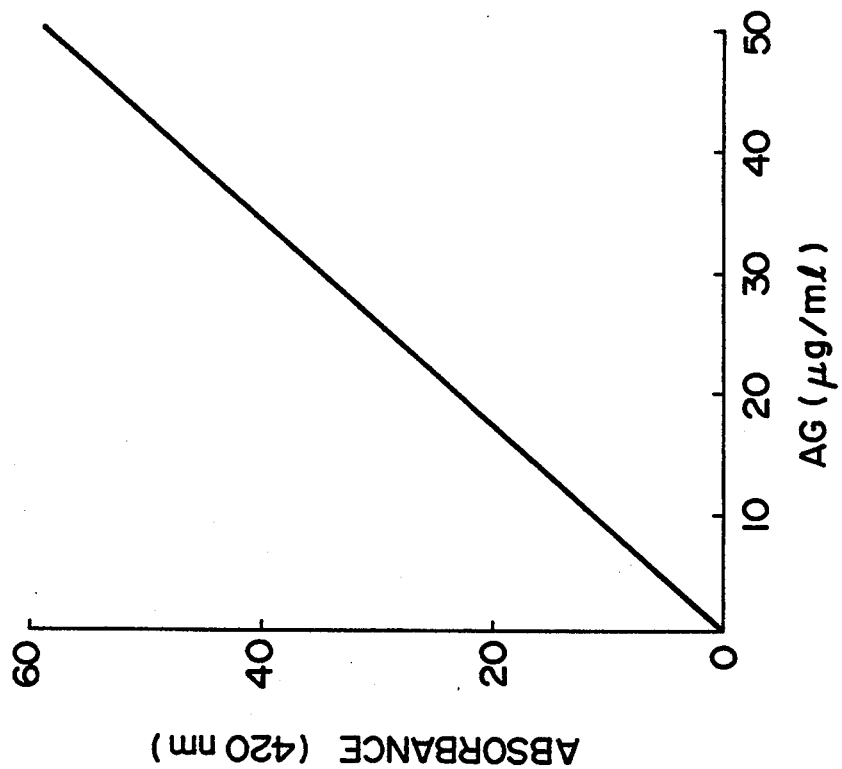
FIG. 1—1 shows an AG calibration line obtained by using pyranose oxidase.

The test samples to be used in the present invention, which are expected to contain proteins and saccharides, include those containing sugar-alcohols such as biological fluids, for example, serum, plasma, urine, or cerebrospinal fluid, and extracts from plant or animal tissue, but not limited thereto.

Sugar-alcohols include straight chain polyhydric alcohols, reductants of from saccharides, anhydro compounds produced through ring closing intramolecular condensation of said alcohols, and cyclic polyhydric alcohols. Among these sugar-alcohols, AG and MI are useful as markers for diagnosing diabetes mellitus in that the patients exhibit a markedly reduced concentraion of AG in the serum and an increased concentraion of MI in the urine, as well known. The term "saccharides" as used here means monosaccharides such as aldose or ketose, and oligosaccharides thereof, not including sugar-alcohols.

In the first embodiment of the present invention, the basic anion-exchange resins having a protein-removing ability and a saccharide-removing ability to be filled into a column are those incapable of removing sugar-alcohols. Such resins are strongly basic anion-exchange resins having quaternary ammonium groups introduced as exchanging groups.

Materials for making said resins are hydrophilic polymer resins having no aromatic ring, for example, hydrophilic gel filtrating resins (polymer gel having molecular sieve function). Hydrophilic gel filtrating resins include polysaccharides such as dextran, agarose, cellulose, and chitosan, and resins such as polyvinyl alcohols, polyethylene glycols, polyacryl amides, poly(meth)acrylic resins, preferably vinyl alcohol or poly(meth)acrylic resins. Quaternary ammonium groups include lower ($C_1$-$C_4$) alkyl ammonium groups such as trimethyl ammonium group, triethyl ammonium group, and hydroxy-lower ($C_1$-$C_4$) alkyl di-lower ($C_1$-$C_4$) alkyl ammonium groups such as hydroxyethyl dimethyl ammonium group. These strongly basic resins may be employed in the ionic form of free base $OH^-$ form, or weak acid salt such as borate form. Preferred resins include Mono Q (available from Pharmacia), Shodex TM (from Showa Denkô), Nucleosil 100-SB (from Nagel), Partisil 10 SAX (from Wattman), Sepralyte SAX, Bond Elute SAX (from Analytical International), QAE-Toyopearl (from Toso), QA-Trisacryl (from IBF), Sepabeads FP-QA (from MITUBISH Chemicals), QAE-Sephadex, Q-Sepharose (from Pharmacia), and QAE-Cellulose (from Chisso). Most preferable resins are QAE-Toyopearl, polyvinyl alcohol resin having trietyl ammonium groups. In case biosensors as described later are employed, one may make mention Shodex TM too, polymethacrylic resin having trimetylammonium groups.

These resins should be used in an Mount of 1 ml or more, preferably 2 to 6 ml per 1 ml of a test sample. These resins may be employed in combination of two or more depending upon the end use, or if the resins have an insufficient capability of removing saccharides, they may be used in combination with any resin having a saccharide-removing ability as described later.

These resins are unstable in their $OH^-$ form to lower their abilities for removing proteins and saccharides during storage for a long period of time. Although the commercially available Cl form of the resins is stable, they must be washed to neutralization after removing the Cl ions using alkali which is undesirably troublesome and time-consuming. The present inventors have discovered that the borate form of the resins has an increased stability and requires only washing with water in use. That is, the aforementioned resins of the OH or borate forms are immersed in such an amount of an aqueous solution of boric acid of a concentration of 0.05 to 1M as no part of the resins being exposed above the liquid surface, thereby preventing a drop of the performances of the resins at least for one year. Therefore, by preparing columns packed with said resins and filled with aqueous solution of boric acid, the quantitative determination of the present invention can be easily performed.

As these resins have an ion-exchange function, ionic substances in samples, if present, effect ion-exchanging and render the effluent alkaline. For adjustment of pH, strong cation-exchange resins may be incorporated, for example, introduced to fill the lowest part of the column. For example, ion-exchange resins having sulfonic acid introduced such as AG 50W-X8 (available from Bio-rad Co.), and Amberlite CG-120 Type 1 (available from Rome & Haas Co.) may be employed.

The first embodiment of the present invention may be carried out, for example, as follows: 50 to 100 $\mu l$ of a test sample itself are passed through the aforementioned column, the column is washed with 0.5 to 1.0 ml of water two or three times, the resulting effluent is quantitatively measured for the sugar-alcohols recovered quantitatively therein by any conventional method such as gas chromatography or enzymatic oxidation. Depending upon the type of quantitative determination method, there are some cases where the proteins and saccharides, particularly proteins, need not be all removed, but need to be only removed to such a degree as to not interfere with the quantitative determination.

Enzymatic process will be explained under. Enzymes reactive specifically with sugar-alcohols to be measured are employed. For example, if AG in serum is measured, AG oxidases such as pyranose oxidase and L-sorbose oxidase may be used to produce hydrogen peroxide owing to oxidation reaction. All that needs to be done is to detect the evolved hydrogen peroxide by various methods. If MI in urine is measured, MI dehydrogenases are used with corresponding coenzymes, $\beta$-nicotinamide adenine dinucleotide (NAD), or $\beta$- nicotinamide adenine dinucleotide phosphate (NADP). All that needs to be done is to detect the NADH, or NADPH produced by the enzymic reduction of each of the coenzymes.

The quantitatively determining method will be further explained in detail. For example, in the case of AG, the following procedure may be conducted. First, in the presence of oxygen, pyranose oxidase, or L-sorbose oxidase are added to a sample in an amount of 0.5 to 10 units, preferably 1 to 5 units per 1 ml of sample, incubated at a temperature of 4° to 50° C., preferably 4° to 37° C. for 0.5 to 3 hours, preferably 0.5 to 1 hour, then measured for an amount of hydrogen peroxide generated, and determined for an amount of AG with the calibration line previously prepared. The method may be actually conducted as follows.

As a method for detecting hydrogen peroxide according to the present invention, one may employ any one of many methods as long as it has a high sensitivity to detection. Most popular one among them is to oxidize various horse radish peroxidase (HRP) substrates with hydrogen peroxide using HRP as a catalyst enzyme. The coloring matters, fluorescent substances, or chemical luminescence generated due to the oxidation reaction are measured by absorbance, fluorescence, or luminescence, respectively. Substrates of HRP capable of producing colors include 2,2'-azinobis(3-ethylbenzothiazoline-6-sulfonic acid) (ABTS), o-phenylene diamine (OPD), 5-aminosalicylic acid (5-AS), 3,3', 5,5'-tetramethylbenzidine (TMB), and couple of 4-aminoantipyrine and various thorinder reagents. Thorinder reagents include phenol derivatives such as phenol, and 3-hydroxy-2,4,6-triiodo benzoic acid (HTIB), aniline derivatives such as N-ethyl-N-(2-hydroxy-3-sulfopropyl)-m-toluidine (TOOS), and 3,5-dimethoxy-N-ethyl-N-(2-hydroxy-3-sulfopropyl)aniline (DAOS).

Substrates of HRP capable of producing fluorescent substances include p-hydroxyphenyl acetic acid, and 3-(p-hydroxyphenyl)propionic acid (HPPA). Chemically luminescent HRP substrates include luminol, and isoluminol as known. An example of practical procedures may be as follows.

0.3 ml of sodium phosphate buffer solution (1/15M, pH 5.6), 0.5 ml of a chromogenic liquor comprising 4 mM ABTS and 12 units/ml HRP, 0.1 ml of a solution of pyranose oxidase, or L-sorbose oxidase 25 units/ml and 0.1 ml of AG solution are charged in a vessel, reacted at a temperature of 25° C. for one hour, and measured for absorbance at 420 nm. A concentration of AG can be determined from the absorbance of the sample by calculation with the calibration line which has been previously prepared using a known concentration of AG.

Some methods of detection by means of chemical luminescence without HRP have been known. For example, those using luminescence of luminol with hydrogen peroxide in the presence of ferricyan ions, luminescence of lucigenin with hydrogen peroxide in the presence of metal ions, luminescence of fluorescent substances excited with the energy generated from decomposition of an oxalate ester, for example, any one of aryl oxalate ester compounds such as bis(2,4,6-trichlorophenyl)oxalate through reaction with hydrogen peroxide in the presence of the fluorescent substances have been known. Moreover, as a method of detecting directly hydrogen peroxide, hydrogen peroxide electrodes may be employed.

For example, in the case of MI, the following may be performed. A coenzyme and 0.1 to 10 units, preferably 0.5 to 5 units of myoinositol dehydrogenase per 1 ml of a sample are added to an effluent out of the column, incubated at a temperature of 4° to 50° C., preferably 25° to 40° C. for 0.5 to 3 hours, preferably 0.5 to 2 hours, then measured for the coenzyme reductant, and determined for the MI level using the previously prepared calibration line.

As a method for detecting the coenzyme reductants, for example, NADH and NADPH to be used in the present invention, one may employ any one of a number of methods, as long as it has a high sensitivity to detection. Most popular one among them is to measure absorbances or fluorescent strengths of the reductants themselves. Alternatively, the produced coenzyme resultants may be air-oxidized in the presence of electron-transfers such as phenazine methosulfate, 1-methoxy-5-methylphenazium methylsulfate, and methylene blue to produce hydrogen peroxide which may be detected by any one of aforementioned methods. Practically, the following procedure may be carried out.

1.0 ml of a 40 mM sodium carbonate buffer solution containing 140 mM ammonium sulfate (pH 9.0), 0.2 ml of a 7 mM NAD solution, 0.2 ml of a solution of myoinositol dehydrogenase 10 units/ml, 0.4 ml of distilled water, and 0.2 ml of a MI solution are charged in a vessel, reacted at a temperature of 25° C. for 2 hours, and thereafter measured for the fluorescent strength at an exciting wavelength of 365 nm and a detecting wavelength of 450 nm. A concentration of MI can be determined from the fluorescent strength of the sample using the calibration line which has been previously obtained with known concentrations of the MI solutions.

The kit in according to the present invention comprises in combination a column filled with basic anion-exchange resins and a solution of boric acid, said resins having a protein-removing ability and a saccharide-removing ability, a reagent set for determing quantitatively sugar-alcohols consisting of an enzyme for quantifying and a reagent for detecting sugar-alcohols, and a sugar-alcohol for preparing calibration lines. The column is a disposable compact column having an upper layer filled with strongly basic anion-exchange resins which comprises hydrophilic gel filtrating resins having quaternary ammonium and capable of removing proteins and saccharides, and a lower layer filled with cation-exchange resins. An amount of resins filled in the column to be used per one sample may be, for example, as follows:

| | |
|---|---|
| Strongly basic anion-exchange resins composed of hydrophilic gel filtrating resins (OH form or borate form) | 0.1 to 2.0 ml |
| Cationic exchange resins | 0.01 to 0.5 ml |
| Subtotal | 0.5 to 2.0 ml |
| Boric acid solution | 0.5 to 10 ml |
| Total | 1 to 12 ml |

The enzymes for quantitating sugar-alcohols are not critical, for example, in the case of AG, as far as they can be directly used for quantitative determination of AG. For example, one may mention pyranose oxidase and L-sorbose oxidase as described above. Again, in the case of MI, the enzymes for quantitating MI are not critical, as far as they can be directly used therefor. For example, one may mention myoinositol dehydrogenase as described above.

The reagents for quantitating sugar-alcohols where the quantity of the evolved hydrogen peroxide is determined for the quantification are exemplified by combinations of a peroxidase or a peroxidase-like active substance and a chromogenic substrate or a color-developing agent and a coupler, a peroxidase and a fluorescent substrate, a peroxidase and a luminescent substrate, and of ferricyanate ions and a luminescent substrate. Practical examples of the reagents are apparent from the above description on "Methods for detecting hydrogen peroxide".

In case the coenzyme reductants, for example, NADH and NADPH, are determined for the quantification, the coenzymes themselves may be measured for their absorbance, or fluorescence intensity. Alternatively, the coenzyme reductants may be converted to hydrogen peroxide via oxidation with reagents of an electron-transfer allowing the aforementioned hydrogen peroxide-detecting reagents to be used.

Quantity of the enzymes for quantitating sugar-alcohols in the kit may vary depending on the number of measurable samples, for example, 100 test samples, 300 test samples, or the like. When AG is quantitatively determined, about 0.5 to 10 units of enzymes per test sample may be added, and when MI is determined, about 0.1 to 5 units be added. With respect to the reagent sets, in case HRP and ABTS may be used as reagents for detecting hydrogen peroxide, they may be incorporated in a kit in an amount of 0.01 to 0.1 unit of HRP and 1 to 20 $\mu$M of ABTS per test sample. If the method for detecting the coenzyme reductants is to measure their fluorescence strength, the coenzymes may be incorporated in a kit in an amount of 0.2 to 10 $\mu$M per test sample.

In addition, as reagents for preparing calibration lines, for example, in the case of AG, or MI, each of them should be incorporated in a kit in an amount of 100 to 1000 $\mu$M of each.

Enzymes for quantitating and reagents for detecting AG may be all mixed to produce a single mass, whereas the components may be divided into appropriate combinations when there are any components interfering with one another. These may be prepared in the form of solution, or powdery reagents, which may be further processed to be deposited on appropriate carriers such as filter sheets, or films, allowing to be used as test paper, or analysis films.

The automatic quantification with a biosensor in accordance with the fifth embodiment of the present invention will be discussed hereafter. This method is to inject a sample onto an interfering substance-removing column, through which water or an acidic buffer solution has been flowing, to remove the interfering substances in the sample, and the effluent containing AG is detected directly by the biosensor. Therefore, the apparatus to be used in the present invention comprises essentially an interfering substance-removing column, through which a liquid is allowed to flow by means of a pump, or the like, an injector for introducing a test sample in the column, and a biosensor for detecting AG.

Biosensors to be used in the present invention may be of the flow-cell detector type where a membrane having AG oxidase immobilized is fixed on the surface of a hydrogen peroxide electrode. This type of sensor allows AG passing through the flow-cell to be oxidized with AG oxidase on the surface of the hydrogen peroxide electrode to simultaneously produce hydrogen peroxide which is detected by the hydrogen peroxide electrode to quantify AG. The reactor type of sensor having a small column filled with enzyme-immobilized carriers which is different from the membrane type of immobilized enzyme may be used to permit the simultaneous quantitative determination of AG. Moreover, this reactor type of biosensor can convert AG to hydrogen peroxide which is discharged through the reactor column, allowing the use of an electrochemical detector capable of detecting hydrogen peroxide instead of the hydrogen peroxide electrode.

Immobilization of AG oxidase may be effected by using any one of conventional enzyme-immobilizing methods such as adsorption, crosslinking, and covalent bonding methods. Preferably, one should employ a method which can produce a membrane exhibiting a higher permeability to AG substrate and hydrogen peroxide. In the case of the reactor type, highly liquid-permeable effluent should preferably be employed.

Since the biosensor having a hydrogen peroxide electrode detects electrochemically a redox reaction, if reducing or oxidizing substances coexist in test samples, detection of only AG becomes difficult because such substances cause signals similarly to hydrogen peroxide to be detected. The detection of only AG will be prevented and made impossible by, particularly, ascorbic acid, uric acid, and the like in blood, if present. For this reason, conventionally these substances are prevented from entering by attaching a protective membrane impermeable to them. In contrast with this, the present method allows these interfering substances to be adsorptively removed by using the aforementioned interfering substance-removing column filled with strongly basic anion-exchange resins, and makes it possible to measure the effluent out of the column directly by the biosensor. Although the measurement by the biosensor is not affected, a quantity of proteins is present in test samples and may cover saccharide-adsorbing functional groups in said resins to reduce markedly their treating ability. Therefore, care must be taken to select resins. Preferably, hard resins composed of relatively hydrophilic poly(meth)acrylic resins not having strongly hydrophobic aromatic rings, or hydrophilic polyvinylalcoholic resins, which these resins have quaternary ammonium groups. These resins of the OH$^-$ or borate form can remove components in blood interfering the measurement by biosensor as described above, so that they can provide most suitable interfering substance-removing columns for continuous detection by biosensor. In addition, these resins have ion-exchanging function to render the effluent alkaline due to the ion-exchanging if ionic substances are present in samples. For adjustment of pH, strong cation-exchange resins may be used in combination, for example, ion-exchange resins having sulfonic acid introduced may be employed.

A speed of a flow of liquid passing through the columns depends on the time in contact with the biosensor, and should be carefully selected because sensitivity and measuring time vary with the contacting period of time. When the interfering substance-removing columns have an inside diameter of 4 to 10 mm$\phi$, a flowing rate of 0.1 to 5.0 ml/min. is preferred. In this case, liquid may be allowed to flow downward owing to a difference in pressure, but that is difficult in controlling the flowing rate. Thus, the use of a pump is preferred. Preferably, pumps to be used should have less pulsation, and the cylinder type and the plunger type of pump are excellent. Injectors may be either the cylinder type or the fixed loop type. Preferably, a less variable injector should be employed to enhance reproducibility in the results of measuring test samples having a low AG concentration. Of course, an autoinjector is employed in full automatic systems. An amount of sample to be introduced depends on the measuring sensitivity, and should be prolongation of duration of the interfering substance-removing columns, preferably about 5 to 50 μl. As samples (test samples) to be used in the present invention, protein-unfreed serum or plasma itself may be used. Alternatively, a protein-insolubilizing agent may be added to serum or plasma to produce water-insolubilized ones for use in samples.

Water or a boric acid buffer solution are used as liquid being allowed to flow through the columns. The boric acid buffer solutions of a higher concentration do not cause adsorption in same cases, and therefore, those of a lower concentration are preferred such as 0.2M or less, preferably 0.1M or less, most preferably 0.001 to 0.05M. In this case, the pH of the boric acid buffer solution must be changed depending upon the type of filler in the interfering substance-removing columns. When strong cation-exchange resins are used in combination, boric acid buffer solutions of a higher pH are undesirable due to cation adsorption, and boric acid alone is rather preferably used. When only strong cation-exchange resins are used, any pH may be selected because cations can pass through. Most suitable pH for the enzyme of the biosensor, for example, pH of 5 to 9 may be selected. Since water or a boric acid solution of a low concentration have a small buffering action, ionic substances in samples are subjected to ion-exchange in the interfering substance-removing columns to cause pH variation. Therefore, the most suitable pH for enzyme reaction can not be maintained to reduce the durability of the enzyme membrane of the biosensor, or to cause in some cases noises and shocks. In order to maintain the most suitable pH, a buffer solution having a strong buffering action may be mixed after passing through the interfering substance-removing columns resulting in enhancement of the durability of the biosensor. The buffer solutions to be used here are not critical, as far as they can maintain the most suitable pH for AG oxidase, for example, pH 5 to 9, one may mention phosphoric acid buffer solutions.

Preferred measuring method according to the present invention comprises passing distilled water or a boric acid buffer solution of a low concentration through an autoinjector, an interfering substance-removing column, and a biosensor of the hydrogen peroxide electrode type attached with a AG oxidase immobilized membrane, where a mixing joint is disposed between the interfering substance-removing column and the biosensor to add a phosphoric acid buffer solution and connected to the biosensor via a mixing coil. The biosensor is connected to a recording means, or a data processing equipment to convert signals from the hydrogen peroxide electrode to peaks which are quantitatively analyzed from their areas or heights. A standard AG and sample serum or plasma are injected by the injector into the interfering substance-removing column, and only AG in the effluent therefrom is quantitatively determined as an amount of hydrogen peroxide by the biosensor. With the standard AG, calibration lines are made to quantify the AG in a sample on the basis of the calibration lines.

In the next place, the fourth embodiment of the present invention will be explained.

The protein-insolubilizing agents for producing oily precipitates used the fourth embodiment ① are for precipitating proteins as oily precipitates by addition of the agents allowing the protein-freed supernatant to be obtained without centrifugal operation. For example, acrinol may be used. It may be used in an amount of about 2 to 50 mg, preferably 5 to 20 mg per 1 ml of test sample, and preferably added to the test body in the form of an aqueous solution.

Protein-insolubilizing agent-adsorbing resins are not critical, as long as they can adsorb excess protein-insolubilizing agent added for removing proteins. In case acrinol is used, hydrophobic resins such as Diaion HP-22 SS (available from Mitsubishi Chemicals) are preferred. These protein-insolubilizing agent-adsorbing resins may be added into the upper portion of basic anion-exchange resins, thereby permitting simultaneously both removal of the protein-insolubilizing agent and saccharides.

The basic anion-exchange resins are primarily for removing saccharides, and used in the form of $OH^-$ or borate. In the process using the $OH^-$ form of anion-exchange resins, test samples are allowed to flow slowly on the $OH^-$ form of strongly basic resins to adsorptively remove saccharides. Preferred strongly basic resins are those containing quaternary ammonium salts as exchanging groups, including anion-exchange resins having strongly basic trimethylamino group (type I), or hydroxyethyl dimethylamino group (type II), and anion-exchange resins having triethylamino group (QAE-resin). This process is influenced by the velocity of the liquid to be treated flowing on the resins. Therefore, preferably the resins should have a finer grain size (200 to 400 mesh), and the liquid should be allowed to pass slowly. Moreover, the liquid may be treated with cation-exchange resins to neutralize.

The cation-exchange resins are the H type of various anion-exchange resins. Anion-exchange resins include any types of cation-exchange resins from strongly acidic cation-exchange resin to weakly acidic one. Particularly, the H type of strongly acidic cation-exchange resins having a sulfonic acid group are preferred.

The method using the borate type of anion-exchange resins removes adsorptively saccharides as a complex with boric acid. They are not critical, as far as they are of the borate type of anion-exchange resin, including any types of anion-exchange resins from strongly basic anion-exchange resin to weakly basic one. Specifically preferred ones are the borate type of strongly basic anion-exchange resins having trimethylamino group (type I), the borate type of strongly basic anion-exchange resins having hydroxyethyl dimethylamino group (type II ), the borate type of anion-exchange resins having triethylamino group (QAE-resin), and the borate type of moderately basic resins having two types of ion-exchanging groups, dimethylamino group and hydroxyethyl dimethylamino group (Biorex 5, available from Biorad Co.). In order to readsorb borate ions released during treatment of test samples, an additional treatment with anion-exchange resins may be employed. Moreover, in order to neutralize the treated liquid, an additional treatment may be effected.

The anion-exchange resins are of the OH or weak acid salt type of various cation-exchange resins. Cationic resins include any types of anion-exchange resins from strongly basic anion-exchange resin to weakly basic one. Weak acids forming the weak acid salt type of cation-exchange resins are preferably organic acids such as carbonic acid, formic acid, acetic acid, and the like. Specifically preferred cation-exchange resins are strongly basic anion-exchange resins having trimethylamino group (type I), or hydroxyethyl dimethylamino group (type II).

Cation-exchange resins include those as described above.

In case a combination of a variety of resins is required to remove interfering substances, primarily saccharides, all the resins may be introduced into a column to form a multilayer with each layer comprising one kind of resin, or to form a mixed layer. When a column is filled with the resins in the form of multilayer, preferably saccharide-removing resins fill in upper layer, while neutralizing resins fill in lower layer.

The fourth embodiment-① of the present invention can be carried out by adding to test samples a protein-insolubilizing agent to precipitate proteins as oily precipitate, thereafter passing the supernatant through the aforementioned column, washing the column with water, and then quatifying sugar-alcohols in the effluent.

Protein-precipitating agents used in the fourth embodiment-② of the present invention include strong acids such as trichloroacetic acid, perchloric acid, sulfuric acid, hydrochloric acid, and the like. An amount of the protein-precipitating agents to be added is 0.5 to 10% depending upon the type and a quantity of a test Sample and a protein-denaturizing agent. When sodium dodecylbenzenesulfonate (referred to as SDS hereafter) is added to serum, an optimum amount of trichloroacetic acid to be used is 2 to 6%. The protein-modifying agents are added for preventing the proteins precipitated with the precipitating agents from redissolving, and include SDS, sodium tungstate, sodium molybdate, benzylalcohol. Among them SDS is more preferred. An amount of SDS to be added, if used, should be sufficient to completely denature the proteins in test samples. For serum, it is 0.2 to 5%, preferably 0.5 to 2%.

The protein-denaturizing agents and the protein-precipitating agents are prepared in the form of a solution each for two, and may be sequentially added to a test sample, or mixed to form a mixture which is added at a time, if desired.

Basic anion-exchange resins to be filled in a column may be the same as those used in the fourth embodiment-① of the present invention, and may be used in combination with cation-exchange resins as neutralizing agents.

The fourth embodiment-② of the present invention can be performed by adding to test samples a protein-denaturizing agent and a precipitating agent to convert proteins to water-insoluble precipitate, then passing the whole as it is without subjecting to centrifugal separation through a column filled with the resins, washing the column with water, and thereafter, quantitating sugar-alcohols in the effluent. Columns to be used in this step are not critical, insofar as they can filtrate the insolubilized proteins to remove the same. Preferably, a filter such as filter paper, sintered polyethylene resin sheets made from polyethylene resins which have been treated to render the surfaces thereof hydrophilic, and the like, may be attached on the top of the resins in the column.

In practicing the fourth embodiment-② of the present invention, an amount to be used per test sample is, for example, as follows:

| | |
|---|---|
| Protein-denaturizing agent: | 2-20 µg |

-continued

| | |
|---|---|
| SDS | |
| Precipitating agent: | 5-30 µg |
| trichloroacetic acid | |
| Column: | |
| Filter sheet | one or more |
| Strongly basic anion-exchange resin (OH⁻ form) | 0.1-1.0 ml |
| Cation-exchange resin | 0.01-0.5 ml |
| Total | 0.2-1.5 ml |
| or | |
| Filter sheet | one or more |
| Strongly basic anion-exchange resin (borate form) | 0.1-0.5 ml |
| Strongly basic anion-exchange resin (OH⁻ form) | 0.1-1.0 ml |
| Cation-exchange resin | 0.01-0.5 ml |
| Total | 0.5-2 ml |

In practicing the fourth embodiment-① of the present invention, an amount to be used per test sample is, for example, as follows:

| | |
|---|---|
| Protein-insolubilizing agent for producing oily precipitate: Acrinol | 2-20 µg |
| Column: | |
| Diaion HP-20 SS | 0.1-0.5 ml |
| Strongly basic anion-exchange resin (OH⁻ form) | 0.1-1.0 ml |
| Cation-exchange resin | 0.01-0.5 ml |
| Total | 0.5-2 ml |
| or | |
| Diaion HP-20 SS | 0.1-0.5 ml |
| Strongly basic anion-exchange resin (borate form) | 0.1-0.5 ml |
| Strongly basic anion-exchange resin (OH⁻ form) | 0.1-1.0 ml |
| Cation-exchange resin | 0.01-0.5 ml |
| Total | 0.5-2.0 ml |

The present invention will be practically explained with reference to Experiments and Examples hereinunder.

Experiment 1

(AG calibration line using pyranose oxidase)

In a 0.25M phosphate buffer solution (pH 5.6), pyranose oxidase (specific activity of 5 units/mg to glucose; available from TKARA SHUZÔ) of 2 mg/ml, HRP of 0.24 unit/ml, ABTS of 4 mM were dissolved to prepare an AG detecting solution. 2 ml of water were added to 0.1 ml of an AG standard solution to produce an AG solution, to which 0.5 ml of the AG detecting solution was added and reacted at a temperature of 25° C. for one hour. This reaction liquid was measured for absorbance at 420 nm to obtain a calibration line which is shown in FIG. 1-1.

Experiment 2

(AG calibration line using L-sorbose oxidase)

The reaction in Experiment 1 was repeated, except that pyranose oxidase was replaced by L-sorbose oxidase (specific activity of 4.3 units/mg to glucose) to prepare an AG calibration line. The result is shown in FIG. 1-2.

Experiment 3

(MI calibration line using myo-inositol dehydrogenase)

Figures 1, 2, 3, 4:
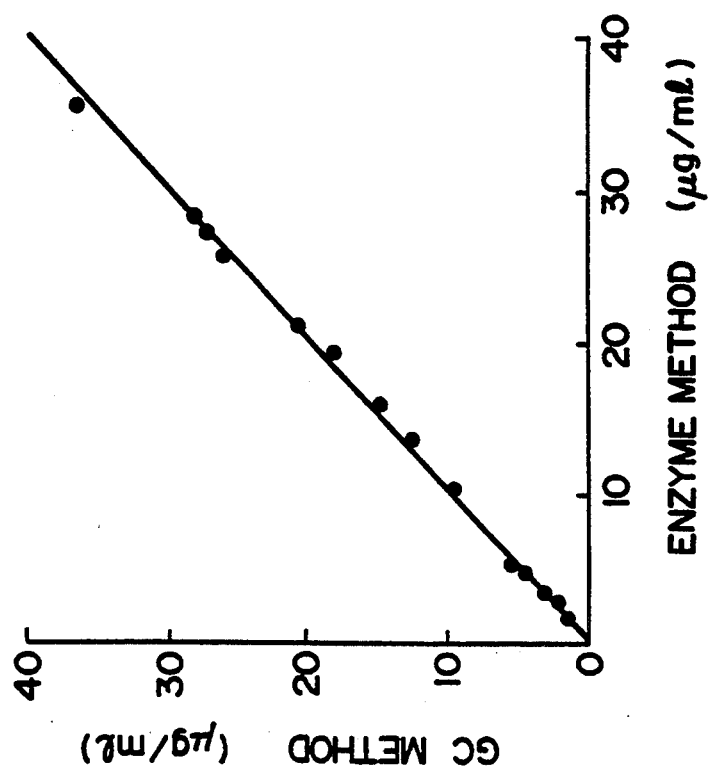
Figures 1, 2, 3:
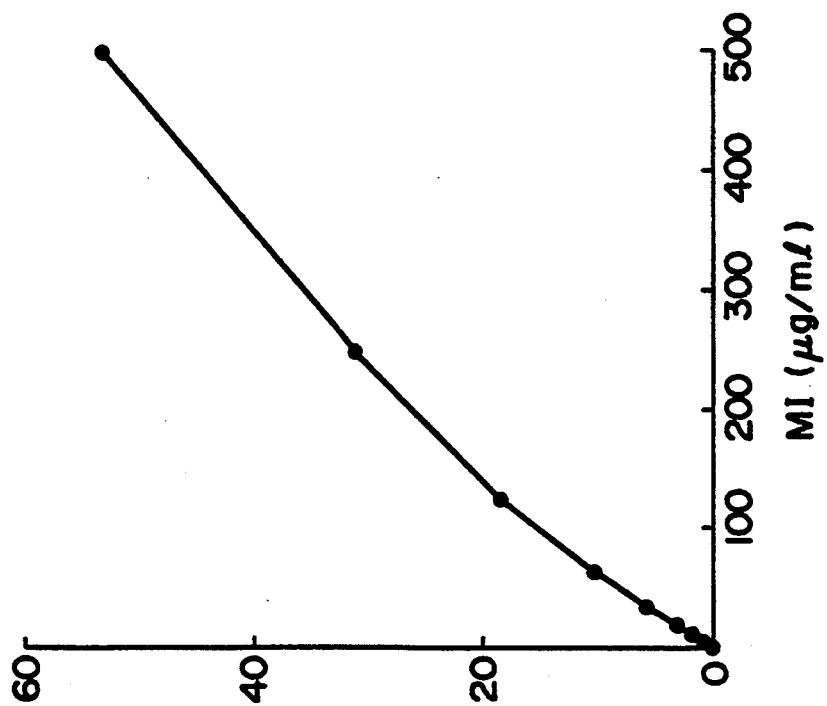
Figures 1, 2, 3, 4, 5, 6:
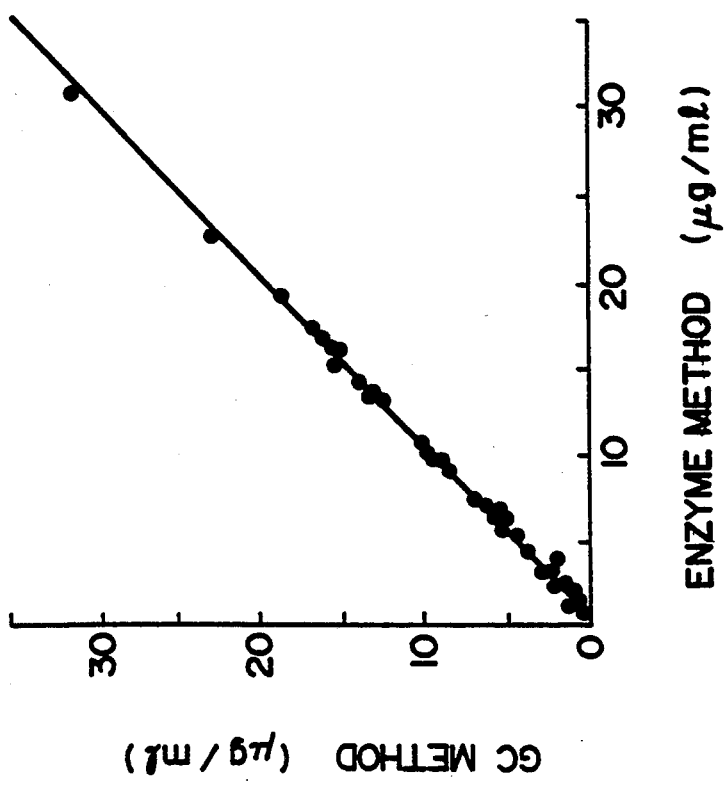
Figures 1, 2, 3, 4, 5:
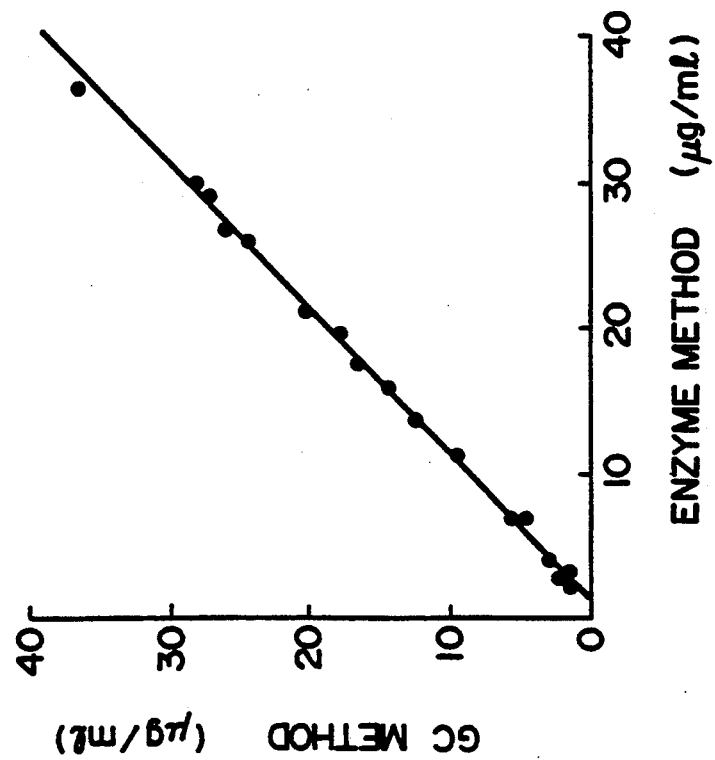
Figure 2:
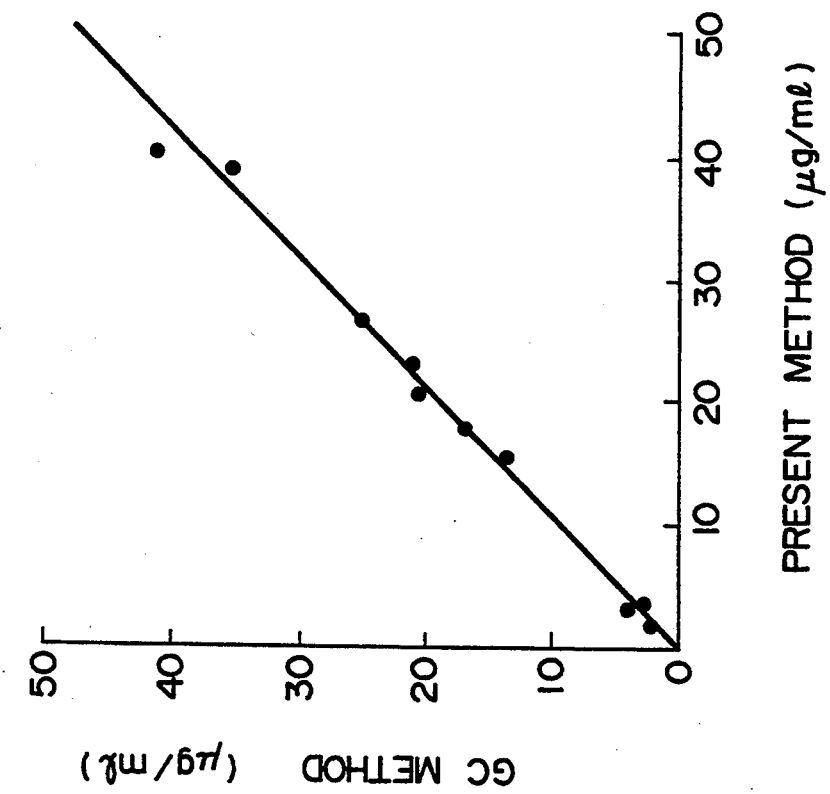
Figures 1, 2:
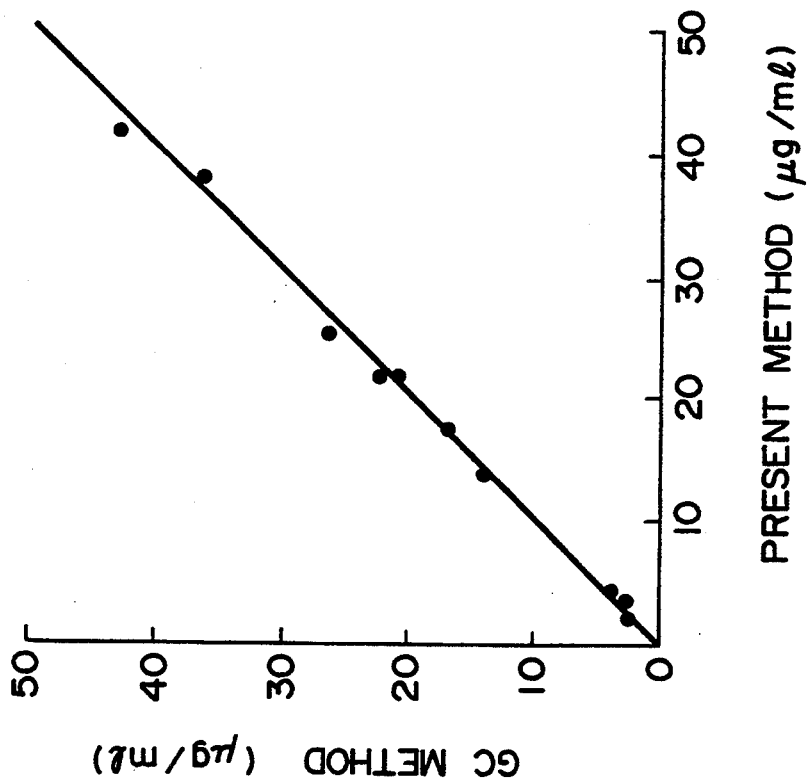
Figures 2, 3:
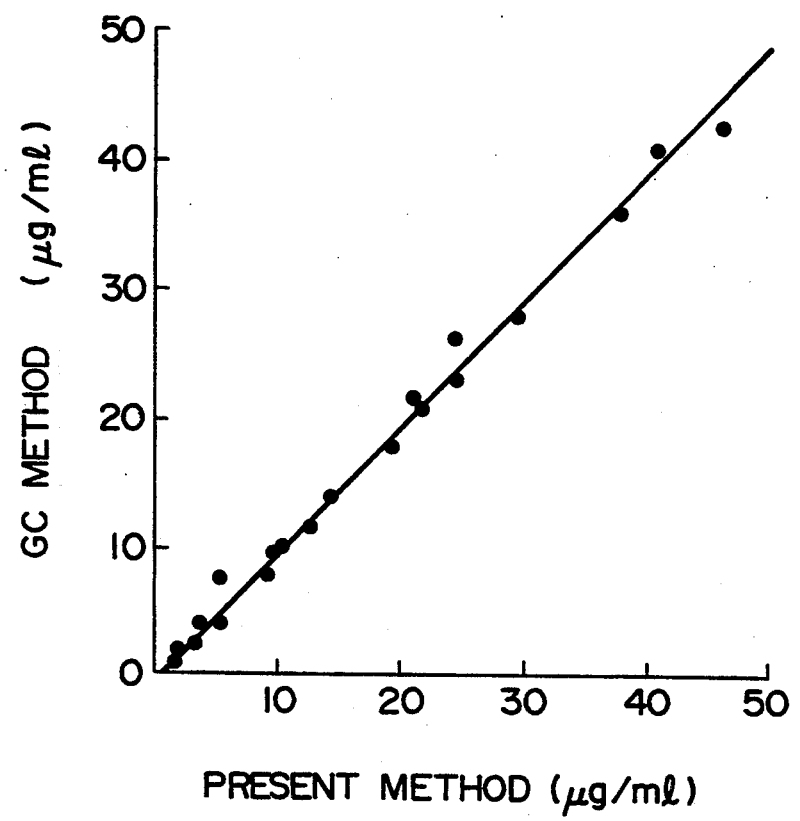

In a 20 mM sodium carbonate buffer solution containing 70 mM ammonium sulfate (pH 9.0), myo-inositol dehydrogenase (10 units/mg, available from Sigma Co.) and NAD were dissolved to attain concentrations of 1 unit/ml and 1 mM, respectively, to prepare a MI detecting reagent. To 0.1 ml of a MI standard solution, 0.9 ml of the MI detecting reagent was added, and reacted at a temperature of 25° C. The reaction liquid was measured for fluorescence strength at an exciting wavelength of 365 nm and a detecting wavelength of 450 nm. The result is shown in FIG. 1-3.

EXAMPLE 1-1

(AG determination using pyranose oxidase)

Serum test samples were subjected to the pretreatments as described in Examples 1-4 to 1-6 later to remove saccharides, and was measured for the remaining AG by the same process as described in Experiment 1. The quantitative determination of AG was accomplished on the basis of the calibration line obtained by pretreating each AG standard solution in the same method as for the serum test samples. The results are shown in Table 1. Example 1-2 (AG determination using L-sorbose oxidase)

The same serum test samples as used in Example 1-1 were subjected to the pretreatments as described in Examples 1-4 to 1-6 later to remove saccharides, and was measured for the remaining AG by the same process as described in Experiment 2. The quantitative determination of AG was accomplished on the basis of the calibration line prepared by pretreating each AG standard solution in the same method as for the serum test samples. The results are shown in Table 1.

TABLE 1

Results of determination of AG in serum test samples

| Saccharides removing method | AG measuring enzyme | |
|---|---|---|
| | Pyranose oxidase | L-sorbose oxidase |
| Pretreated by the method in Example 1-4 (First embodiment of the present invention) | 28.1 μg/ml | 28.7 μg/ml |
| Pretreated by the method in Example 1-5 (Fourth embodiment ② of the present invention) | 29.4 | 28.6 |
| Pretreated by the method in Example 1-6 (Fourth embodiment ① of the present invention) | 28.3 | 29.0 |

EXAMPLE 1-3

(MI determination using myoinositol dehydrogenase)

Urine test samples were subjected to the pretreatments as described in Examples 1-7 later to remove saccharides, and was measured for the remaining MI by the same process as described in Experiment 3. The quantitative determination of MI was accomplished on the basis of the calibration line prepared by pretreating a MI standard solution in the same process as for the urine test samples. The results exhibited a good coincidence with those obtained by measurement of the same urine test samples on a gas-chromatography.

EXAMPLE 1-4

(Pretreatment of serum test samples for sugar-alcohols analysis by passing through an interfering substance-removing column containing protein-adsorptive resins)

Ion-exchange resins, AG50W-X8 of the H form and QAE-Toyopearl 550C (available from Tôso) of the borate form were filled sequentially into a small column from the bottom thereof in the form of multilayer in amounts of 0.1 ml and 0.5 ml, respectively, to make a sample-pretreating column. Through this column, is 0.1 ml of human serum directly passed, and then the column was washed four times with distilled water of 0.5 ml each to produce 2.1 ml of the effluent. In illustration, quantitative determination of AG among the sugar-alcohols recovered in the effluent was performed as in Experiment 1. Dependency of the thus obtained measurements upon those by measuring the same test samples on a gas-chromatography is shown in FIG. 1-6.

The above process was repeated, except that QAE-Toyopearl 550C borate form resin was replaced by its OH− form in the column, to obtain the same results as the above.

Furthermore, the above process was repeated, except that the resins filled in the treating column was replaced by a mixture of the AG50W-X H form resin and the QAE-Toyopearl borate form one in a ratio of 1:5, to the same results as the above.

The QAE-Toyopearl resins of the OH− form resin and the borate type were prepared from the commercially available Cl− form by the following procedure. That is, 250 ml of QAE-Toyopearl 550C (Cl− type) resin were filled in a column, 1 l of a 0.2M sodium hydroxide solution was allowed to slowly flow through the column to elute out Cl− ions, and the column was washed with distilled water until the effluent became neutral to produce the OH− form resin. Into this OH− form resin, 3 l of a 0.5M boric acid solution was introduced flowing slowly from the top of the resin to acidify until pH of the effluent became acidic. Then, the resin was washed with distilled water until the effluent became neutral to obtain the borate form resin.

The AG50W-X8 H type resin was prepared from the commercially available Na+ form by the following procedure. That is, 200 ml of AG50W-X8 (Na+ form) resin were filled in a column, 1 l of a 1M hydrochloric acid solution was allowed to flow slowly through the column to elute out Na+ ions, and the column was washed with distilled water until pH of the effluent became neutral.

EXAMPLE 1-5

(Pretreatment of serum test samples for sugar-alcohols analysis by passing through an interfering substance-removing column with a filter and an irreversibly protein-insolubilizing agent)

Ion-exchange resins, AG50W-X8 of the H form and AG1-X8 of the OH− form (both available from Bio-rad Co.) were filled sequentially into a small column from the bottom thereof in the form of multilayer in amounts of 0.1 ml and 0.4 ml, respectively, and a sintered filter of hydrophilic polyethylene is disposed on the top of the resins filled in the column to make a sample-pretreating column.

0.1 ml of a 5% SDS solution was added to 0.2 ml of human serum, shaken, and then 0.1 ml of a 12% trechloroacetic acid solution was added, and strongly shaken. 0.2 ml of the resulting dispersion containing precipitate was passed through the sample-pretreating column as described above, and the column was washed four times with distilled water of 0.5 ml each to produce 2.2 ml of the effluent. Quantitative determination of AG among the sugar-alcohols recovered in the effluent will be illustrated under. The determination of AG was effected by the process as described in Experiment 1. That is, to this AG solution, 0.5 ml of the AG detecting reagent was directly added to react. The quantitating AG was accomplished on the basis of the calibration line made by using the AG standard solution. Dependency of the thus obtained measurements of serum AG values of normal human and diabetic patient upon those by measuring the same test samples on a gas-chromatography is shown in FIG. 1-4. It is apparent from this FIGURE that the measurements according to the present invention exhibit an excellent correlation with those by the gas-chromatography without any influence of the presence of a great excess of glucose.

EXAMPLE 1-6

(Pretreatment of serum test samples for sugar-alcohols analysis by treating with a protein-insolubilizing agent capable of producing oily precipitates and passing through an interfering substance-removing column with an insolubilizing agent-adsorbing resin)

Ion-exchange resins, AG50W-X8 of the H form, AG1-X8 of the OH⁻ form (both available from Bio-rad Co.), and hydrophobic resin, Diaion HP-20SS (available from MITSUBISH Chemicals) were filled sequentially into a small column from the bottom thereof in the form of multilayer in amounts of 0.1 ml, 0.3 ml, and 0.1 ml, respectively, to make a sample-pretreating column.

0.2 ml of a 2.5% acrinol solution was added to 0.2 ml of human serum, and shaken. The proteins in the serum were settled as an oily precipitate, and 0.2 ml of the supernatant was passed through the sample-pretreating column as described above, and the column was washed four times with distilled water of 0.5 ml each to produce 2.2 ml of the effluent. In illustration, quantitative determination of AG among the sugar-alcohols recovered in the effluent was conducted in the same way as in Example 1-4. Dependency of the thus obtained measurements upon those by measuring the same test samples on a gas-chromatography is shown in FIG. 1-5.

EXAMPLE 1-7

(Pretreatment of urine test samples for sugar-alcohols analysis by passing through an interfering substance-removing column added with a protein-adsorbing resin)

Ion-exchange resins, AG50W-X8 of the H form and QAE-Toyoperal of the borat type were filled sequentially into a small column from the bottom thereof in the form of multilayer in amounts of 0.2 ml and 1.8 ml, respectively, to make a sample-pretreating column. Through this column 0.5 ml of human urine was directly passed, and then the column was washed eight times with distilled water of 1.0 ml each to produce 8.5 ml of the effluent. Quantitative determination of MI among the sugar-alcohols recovered in the effluent will be illustrated hereunder.

All the aforementioned effluent of 8.5 ml were concentrated to dryness, and redissolved with 0.1 ml of distilled water to produce a solution for treating the pretreated column. Detection of MI was performed as in Experiment 3. That is, to this treating solution, 0.9 ml of the MI detecting reagent was directly added to react. quantitative determination of MI was accomplished on the basis of the calibration line made by using the MI standard solution. Dependency of the thus obtained measurements of MI values in urines of normal human and diabetic patient upon those by measuring the same test samples on a gas-chromatography is summarized in Table 2.

TABLE 2

Results of the measurement of MI values in urines

| Urine test sample | Method for measurement | |
|---|---|---|
| | Use of myoinositol dehydrogenase | Gas-chromatography |
| Normal human | 6.0 μg/ml | 5.7 μg/ml |
| diabetic patient | 177.1 | 174.8 |

EXAMPLE 1-8

(An example of kit for measuring serum AG)

(1) Preparation of kit

AG detecting reagent: 200 mg of PROD (5 units/mg, available from TAKARA SHUZÔ), 0.24 mg of HRP (100 U/Mg, available from WAKÔ JUNYAKU), and 220 mg of ABT (available from Boeringer Co.) were dissolved in 100 ml of an 0.25M sodium phosphate buffer solution (pH 5.6), 16 ml each of the resulting liquor were separately poured into a vial, and freeze-dried by the conventional method.

Restoring liquid: 0.6 g of Triton X-405 (available from WAKÔ JUNYAKU) was dissolved into 100 ml of distilled water, and 16 ml each of the resulting solution was poured into a vial, and the vials were plugged.

Standard solution: 5 mg of AG were dissolved into 100 ml of distilled water, and 3 ml each of the resulting solution was poured into a vial, and the vials were plugged.

Pretreating column: 0.1 ml of AG50W-X H form resin (available from Bio-rad Co.), and 0.5 ml of QAE-Toyopearl borate form resin-(available from Tôso Co.) were filled into Reservoir attached with a frit filter (1.5 ml capacity, available from Analytical International Co.) sequentially from the bottom thereof. A frit filter was disposed and fixed on the top of the resins filled in the column to immobilize the resins. In order to maintain the stability of the filled resins and prevent the resins from drying, the upper part of the column was filled with a 0.2M boric acid solution, and the outlet was closed with a cap, and the inlet was sealed.

(2) Operation

The cap and the seal of the pretreating column were removed, the boric acid solution in the Reservoir was discharged, and furthermore, the column was washed twice with 1 ml of distilled water to purge completely an excess of boric acid out of the resins. This washed pretreating column was set on a test tube, 100 μl of a serum test sample were passed directly through the column which was then washed four times with 0.5 ml of distilled water to produce 2.1 ml of the effluent. The AG detecting reagent in one vial was restored with the restoring liquid in one vial, 0.5 ml of the resulting solution was added to 2.1 ml of the effluent out of the pretreating column, and reacted at a temperature of 25° C. for one hour. The reaction liquid was measured for absorbance at 420 nm by means of a conventional spectrophotometer. Moreover, a series of diluted standard solutions were prepared by conducting in sequence dilution of an amount of a standard solution with the same amount of distilled water to produce a next standard solution having a half concentration, and were subjected to reaction by treating as in the case of serum test samples, whereby AG calibration lines were made. AG concentrations in serum test samples were calculated with absorbance values of the test samples on the basis of the calibration lines. The use of the kit produced the same results as those in Example 1-4.

EXAMPLE 2-1

A 0.05M boric acid buffer solution (pH 5.8) was pumped to flow at a rate of 0.5 ml/min, and the measurement was accomplished by a system comprising an autoinjector, an interfering substance-removing column, a biosensor, and a data-processing apparatus.

The biosensor used comprised Flow-cell (capacity of about 100 μl) having a hydrogen peroxide electrode (available from Eible Inc.), on the surface (5 mm $\phi$) of which a PROD-immobilized membrane of the same size as that of the surface was fixed with a nylon net. The PROD-immobilized membrane was prepared by the following procedure: 10 mg of PROD (5.4 U/mg, available from TAKRA SHUZÔ Inc.) and 6 mg of cow serum albumin (available from Sigma Co. ) were dissolved into 0.6 ml of 1/15M phosphoric acid buffer solution (pH 7.2), and mixed with an addition of 0.2 ml of a 1% aqueous glutaraldehyde solution. Immediately after mixing, the resulting solution was gradually dropped on two nitrocellulose films (25 mm $\phi \times 3$ $\mu$m in pore size), spread uniformly throughout, and air-dried at a temperature of 4° C. over night.

The interfering substance-removing column comprised a column of 5 mm $\phi \times 100$ mm filled with a mixture of polyvinylalcohol resin, QAE-Toyopearl 550C (available from Tôso Inc.) which had been converted to the borate type through the OH type by a conventional method, and strong cation-exchange resin, AG50W-X8 of the H form (available from Biorad Co.) in a ratio of 5:1.

With this system, AG standards of 1, 10, and 40 $\mu$g/ml, and thereafter, 10 serum samples were aligned on the autoinjector (20 $\mu$l fixed loop), and then the measuring was started. The data-processing apparatus produced calibration lines with AG standard areas and gave quantitative measurements of AG in the samples. Dependency of the measurements upon those obtained by measuring the same test samples on a gas-chromatography is shown in FIG. 2-1. As can clearly be seen from this FIGURE, the quantitative measurements in accordance with the present invention exhibited an excellent linearity with those by the gas-chromatography.

EXAMPLE 2-2

The measuring system comprised two pumps, an autoinjector, an interfering substance-removing column, biosensor, and a data-processing apparatus in connection with the biosensor, which were connected to allow the following. Water was allowed to flow at a rate of 0.5 ml/min through the interfering substance-removing column connected with the autoinjector, and the effluent out of the column was mixed with a 0.5M phosphoric acid buffer solution supplied at a rate of 0.1 ml/min in a mixing joint to produce a mixture which was further completely mixed in a mixing coil (1.0 mm $\phi \times 3$ mm). The mixture entered Flow-cell of the biosensor similar to that in Example 2-1.

The interfering substance-removing column used comprised a column of 5 mm $\phi \times 100$ mm filled with QAE-Toyopearl 550C (borate type).

With this system, the measuring was performed as in Example 2-1. Dependency of the measurements upon those obtained by measuring the same test samples on a gas-chromatography is shown in FIG. 2-2. As can clearly be seen from this FIGURE, the quantitative measurements in accordance with the present invention exhibited an excellent linearity with those by the gas-chromatography.

EXAMPLE 2-3

The measuring system was similar to that in Example 2-2. A 0.01M boric acid buffer solution (pH 6.0) was allowed to flow at a rate of 1.0 ml/min through the interfering substance-removing column, and a 1.1M phosphoric acid buffer solution (pH 5.8) was supplied at a rate of 0.1 ml/min at another inlet into the column.

The interfering substance-removing column used comprised a column of 5 mm $\phi \times 100$ mm filled with acrylic resin, Shodex TM-L (available from SHOWA DENKÔ Inc.)(borate form).

With this system, 20 serum samples were measured as in Example 2-1. Dependency of the measurements upon those obtained by measuring the same test samples on a gas-chromatography is shown in FIG. 2-3. As can clearly be seen from this FIGURE, the quantitative measurements in accordance with the present invention exhibited an excellent linearity with those by the gas-chromatography.

As apparent from the above, the process of the present invention allows the interfering substances in test bodies such as proteins and saccharides to be easily removed, the measurement of sugar-alcohols to be extremely simplified. Although certain sugar-alcohols have specificity, it has been found that even such enzymes as reacting widely with saccharides can be sufficiently useful for quantitative determination, if the pretreatment for removing saccharides in accordance with the present invention is incorporated.

What is claimed is:

1. A method for quantitatively determining one or more sugar-alcohol comprising passing test samples containing sugar-alcohols, proteins, and saccharides through a column packed with a basic anion-exchange resin or resins which are hydrophilic polymer resins having a quaternary ammonium group and no aromatic ring, are in the ionic OH− or borate form, and which have a protein removing ability and a saccharide-removing ability, and then quantitating one or more sugar-alcohol in the effluent out of the column.

2. A method according to claim 1, wherein the hydrophilic polymer resin or resins having no aromatic ring are hydrophilic gel filtrating resins.

3. A method according to claim 2, wherein the hydrophilic gel filtrating resin or resins are polymethacrylic resin or resins, polyvinylalcohol resin or resins, polyethyleneglycol resin or resins polyacrylamide resin or resins, or polysaccharide resin or resins.

4. A method according to claim 1, wherein the quaternary ammonium group is tri-lower ($C_1$-$C_4$) alkyl ammonium groups or hydroxy lower ($C_1$-$C_4$) alkyl di-lower ($C_1$-$C_4$) alkyl ammonium groups.

5. A method according to claim 1, wherein the basic anion-exchange resin or resins are polyvinylalcohol hydrophilic gel filtrating resin or resins or polymethacrylate hydrophilic gel filtrating resin or resins having tri-lower ($C_1$-$C_4$) alkyl ammonium groups introduced as exchanging groups and being of the ionic form selected from the group consisting of OH− and borate form.

6. A method according to claim 1, wherein a sugar-alcohol that is quantitated is 1,5-anhydroglucitol.

7. A method for quantitatively determining 1,5-anhydroglucitol which comprises passing test samples containing sugar-alcohols, proteins and saccharides through a column packed with strongly basic anion-exchange resin or resins which are in the ionic OH− or borate form and are selected from the group consisting of polyvinylalcohol hydrophilic gel filtrating resin or resins and polymethacrylate hydrophilic gel filtrating resin or resins having tri-lower ($C_1$-$C_4$) alkyl ammonium groups introduced as exchanging groups, and quantitating 1,5-anhydroglucitol in the effluent.

8. A method according to claim 7, wherein the test sample is serum or samples.

9. A method according to claim 7, wherein the method is carried out using 1,5-anhydroglucitol oxidase for said quantitating in the effluent.

10. A kit comprising a column packed with basic anion-exchange resin or resins which are hydrophilic polymer resin or resins having a quaternary ammonium group and no aromatic ring and which have a protein-removing ability and a saccharide-removing ability and with an aqueous solution of boric acid, or reagents for quantitating one or more sugar-alcohol and one or more sugar-alcohol for preparing calibration lines.

11. A method for determining 1,5-anhydroglucitol in blood comprising injecting sequentially a number of test samples containing sugar-alcohols, proteins and saccharides into a system comprising an interfering substance-removing column through which a liquid is flowing, said column packed with strongly basic anion-exchange resin or resins comprising hydrophilic high molecular weight carrier or carriers having quaternary ammonium groups introduced, but not having any aromatic ring and which are in the ionic $OH^-$ or borate form, an injector, and a biosensor, and quantitating 1,5-anhyroglucitol in the effluent.

12. A method according to claim 11, wherein the flowing liquid is water or a boric acid buffer solution.

13. A method according to claim 12, wherein the boric acid buffer solution has a concentration of 0.1M or less.

14. A method according to claim 12, wherein the boric acid buffer solution is an aqueous solution of boric acid alone.

15. A method according to claim 11, wherein the system is such that the test samples flow through the injector, the interfering substance-removing column, and the biosensor in this order.

16. A method according to claim 15, wherein the biosensor comprises a membrane containing 1,5-anhydroglucitol oxidase.

17. A method according to claim 16, wherein the system is further provided with an inlet for introducing a buffer solution between the interfering substance-removing column and the biosensor to maintain the most suitable pH for 1,5-anhydroglucitol oxidase.

18. A method according to claim 17, wherein the most suitable pH is 5 to 9.

19. A method according to claim 17, wherein the buffer solution is a phosphoric acid buffer solution having a pH of 5 to 9.

20. A method according to claim 11, wherein the hydrophilic high molecular weight carrier or carriers having no aromatic ring are hydrophilic gel filtrating resin or resins.

21. The method according to claim 11, wherein the basic anion-exchange resin or resins are polymethacrylate hydrophilic gel filtrating resin or resins or polyvinylalcohol hydrophilic gel filtrating resin or resins having a tri-lower ($C_1$-$C_4$) alkyl ammonium group.

22. The method according to claim 11, wherein the flowing liquid is an aqueous solution of boric acid having a concentration of 0.05 to 1M.

* * * * *